United States Patent
Wang

(10) Patent No.: US 11,315,263 B2
(45) Date of Patent: *Apr. 26, 2022

(54) MEDICAL IMAGE PROCESSING APPARATUS, MEDICAL IMAGE PROCESSING METHOD, AND MEDICAL IMAGE PROCESSING PROGRAM

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 55 days.

This patent is subject to a terminal disclaimer.

(21) Appl. No.: 16/776,528

(22) Filed: Jan. 30, 2020

(65) Prior Publication Data

US 2020/0175699 A1 Jun. 4, 2020

Related U.S. Application Data

(63) Continuation of application No. PCT/JP2018/026871, filed on Jul. 18, 2018.

(30) Foreign Application Priority Data

Aug. 28, 2017 (JP) .............................. JP2017-163011

(51) Int. Cl.
*G06T 7/33* (2017.01)
*A61B 5/00* (2006.01)
(Continued)

(52) U.S. Cl.
CPC ................ *G06T 7/33* (2017.01); *A61B 5/055* (2013.01); *A61B 6/501* (2013.01); *A61B 6/5229* (2013.01);
(Continued)

(58) Field of Classification Search
USPC ................................................ 382/128, 131
See application file for complete search history.

(56) References Cited

U.S. PATENT DOCUMENTS

| | | | | |
|---|---|---|---|---|
| 6,240,308 B1* | 5/2001 | Hardy | .................. | A61N 5/1031 345/420 |
| 7,426,319 B2* | 9/2008 | Takahashi | ............. | G06T 3/0075 382/294 |

(Continued)

FOREIGN PATENT DOCUMENTS

| | | |
|---|---|---|
| JP | 2011010828 | 1/2011 |
| JP | 2011019768 | 2/2011 |

(Continued)

OTHER PUBLICATIONS

Davatzikos et al. Image Registration Based on Boundary Mapping, Feb. 1996, IEEE Transaction on Medical Imaging, vol. 15, No. 1, (Year: 1996).*

(Continued)

*Primary Examiner* — Ishrat I Sherali
(74) *Attorney, Agent, or Firm* — JCIPRNET

(57) ABSTRACT

A medical image processing apparatus having a processor configured to detect at least four reference landmarks among the left eye, the right eye, the diencephalon, the fornix, the corpus callosum, the left hippocampus, and the right hippocampus from a brain image, performs first registration including registration by similarity transformation using reference landmarks between the brain image and a standard brain image, and perform second registration by nonlinear transformation between the brain image and the standard brain image after the first registration.

15 Claims, 5 Drawing Sheets

(51) Int. Cl.
  *G06T 7/00*   (2017.01)
  *G16H 30/40*  (2018.01)
  *A61B 5/055*  (2006.01)
  *A61B 6/00*   (2006.01)
(52) U.S. Cl.
  CPC ........... *G06T 7/0012* (2013.01); *G16H 30/40* (2018.01); *G06T 2207/10012* (2013.01); *G06T 2207/10088* (2013.01); *G06T 2207/30016* (2013.01)

(56) References Cited

U.S. PATENT DOCUMENTS

| | | | | |
|---|---|---|---|---|
| 7,646,898 | B1* | 1/2010 | Nowinski | G06T 7/33 382/128 |
| 7,787,671 | B2* | 8/2010 | De Leon | G06T 7/143 382/128 |
| 7,903,849 | B2* | 3/2011 | Kimura | G06T 7/30 382/128 |
| 8,041,088 | B2* | 10/2011 | Mallya | A61B 6/032 382/128 |
| 8,675,945 | B2 | 3/2014 | Barnhorst et al. | |
| 8,838,201 | B2* | 9/2014 | Mori | A61B 6/5217 600/410 |
| 9,063,643 | B2 | 6/2015 | Sparks et al. | |
| 9,064,332 | B2* | 6/2015 | Hermosillo Valadez | G06T 11/003 |
| 9,207,845 | B2 | 12/2015 | Carlton et al. | |
| 9,251,596 | B2* | 2/2016 | Rueckert | G06K 9/468 |
| 9,310,985 | B2 | 4/2016 | Blum et al. | |
| 9,501,829 | B2 | 11/2016 | Carlton et al. | |
| 9,662,083 | B2* | 5/2017 | Sakaue | A61B 6/469 |
| 10,342,972 | B2 | 7/2019 | Blum et al. | |
| 10,573,414 | B2* | 2/2020 | Kamali-Zare | A61B 5/7278 |
| 2010/0259263 | A1* | 10/2010 | Holland | A61B 5/055 324/310 |
| 2010/0322496 | A1 | 12/2010 | Liu et al. | |
| 2012/0281900 | A1 | 11/2012 | Rueckert et al. | |
| 2013/0054270 | A1 | 2/2013 | Sparks et al. | |
| 2013/0102877 | A1* | 4/2013 | Mori | G01R 33/5608 600/410 |
| 2014/0149929 | A1 | 5/2014 | Barnhorst et al. | |
| 2016/0143573 | A1* | 5/2016 | Brickman | A61B 5/055 382/131 |
| 2017/0079581 | A1* | 3/2017 | Walczak | A61B 5/055 |
| 2018/0268942 | A1* | 9/2018 | Kamali-Zare | A61B 5/7278 |
| 2019/0350486 | A1* | 11/2019 | Walczak | A61M 5/14 |

FOREIGN PATENT DOCUMENTS

| | | |
|---|---|---|
| JP | 2011514190 | 5/2011 |
| JP | 2013506478 | 2/2013 |
| JP | 2014042684 | 3/2014 |
| JP | 2014518516 | 7/2014 |

OTHER PUBLICATIONS

Yousef et al., Two-Stage Registration of Substructures in Mafnetic Resonance Brain Images, 2009 IEEE 978-1-4244-5654-3/09, pp. 1-4. (Year: 2009).*
Zikic et al., Computational Minimal Deformations: Application to Shape Models, 2008 IEEE 978-1-4244-2243-2/08, pp. 1-8. (Year: 2008).*
Dominic Holland et al., "Subregional neuroanatomical change as a biomarker for Alzheimer's disease", PNAS, Dec. 8, 2009, pp. 20954-20959.
Yakang Dai et al., "aBEAT: A Toolbox for Consistent Analysis of Longitudinal Adult Brain MRI", PLOS One, Apr. 2013, pp. 1-13.
Yoshitaka Masutani et al., "201A Non-rigid body deformation by eigen-analysis of point-group displacement in brain MRI and RBF interpolation and its application to standardization", Japanese Journal of Magnetic Resonance in Medicine, Sep. 28, 2005, with English translation, pp. 1-4.
Kouhei Harada et al., "Automatic Registration of Head CT and MR Images Using an ICP Algorithm", Medical Imaging Technology, Sep. 2008, with English abstract, pp. 1-5.
"International Search Report (Form PCT/ISA/210) of PCT/JP2018/026871," dated Oct. 9, 2018, with English translation thereof, pp. 1-5.
"Written Opinion of the International Searching Authority (Form PCT/ISA/237) of PCT/JP2018/026871," dated Oct. 9, 2018, with English translation thereof, pp. 1-7.

* cited by examiner

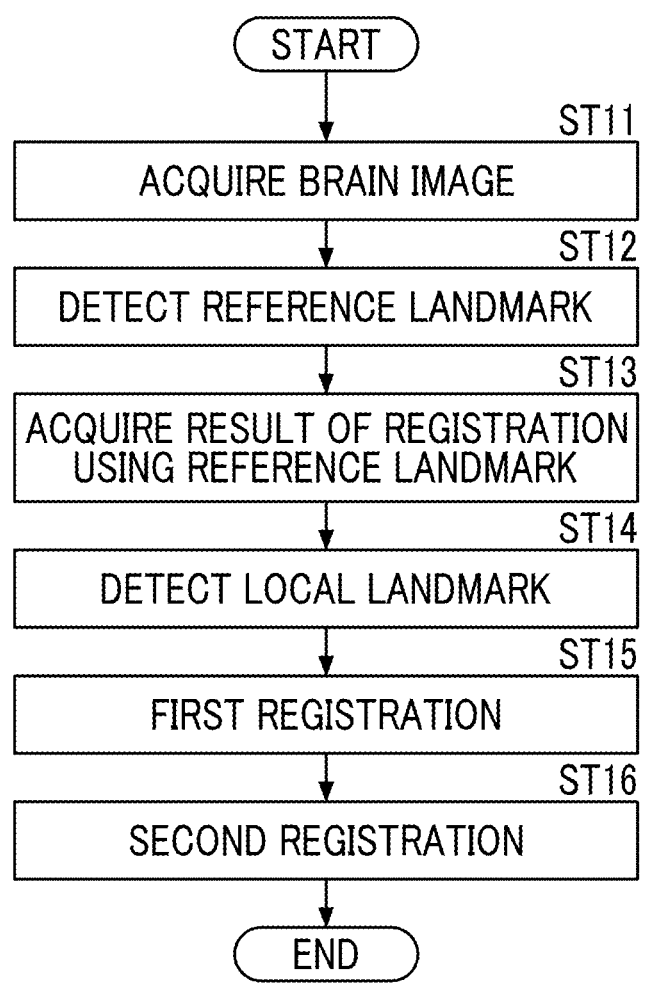

MEDICAL IMAGE PROCESSING APPARATUS, MEDICAL IMAGE PROCESSING METHOD, AND MEDICAL IMAGE PROCESSING PROGRAM

CROSS-REFERENCE TO RELATED APPLICATIONS

This application is a Continuation of PCT International Application No. PCT/JP2018/026871 filed on Jul. 18, 2018, which claims priority under 35 U.S.C. § 119(a) to Japanese Patent Application No. 2017-163011 filed on Aug. 28, 2017. Each of the above application(s) is hereby expressly incorporated by reference, in its entirety, into the present application.

BACKGROUND OF THE INVENTION

1. Field of the Invention

The present invention relates to a medical image processing apparatus, a medical image processing method, and a medical image processing program for performing registration between a brain image of a subject and a standard brain image.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, JP2014-042684A has proposed a method of performing registration between two brain images having different imaging dates and times and then dividing each of the two brain images into tissue regions (gray matter and white matter) and acquiring the amount of change for each tissue region.

On the other hand, for example, a method of performing registration between a brain image of a patient and a standard brain image region-divided according to the Broadmann's brain map and dividing the brain image of the patient into regions has been proposed (refer to JP2011-010828A). Here, the Broadmann's brain map shows which region in the three-dimensional region of the cerebral cortex of the standard brain controls which brain function (motion, language, perception, memory, vision, hearing, and the like). A method has been proposed in which a brain image of a patient is divided into regions and then the amount of change in the volume for each region is acquired (Subregional neuroanatomical change as a biomarker for Alzheimer's disease, Dominic Holland et al., Proceedings of the National Academy of Sciences, Vol. 106, No. 49, pp. 20954-20959, Dec. 8, 2009 and aBEAT: A Toolbox for Consistent Analysis of Longitudinal Adult Brain MRI, Yakang Dai et al., Alzheimer's Disease Neuroimaging Initiative, Apr. 3, 2013). In the methods described in Subregional neuroanatomical change as a biomarker for Alzheimer's disease, Dominic Holland et al., Proceedings of the National Academy of Sciences, Vol. 106, No. 49, pp. 20954-20959, Dec. 8, 2009 and aBEAT: A Toolbox for Consistent Analysis of Longitudinal Adult Brain MRI, Yakang Dai et al., Alzheimer's Disease Neuroimaging Initiative, Apr. 3, 2013, registration between the first brain image of the patient and the standard brain image is performed to divide the first brain image into regions, and registration between the second brain image of the patient, which has a later imaging date and time than the first brain image, and the standard brain image is performed to divide the second brain image into regions. Then, the amount of change in the volume between corresponding regions in the first brain image and the second brain image is acquired.

In addition, a method of performing registration between a brain image and a standard brain image has also been proposed. For example, JP2014-518516A has proposed a method of setting markers on an anatomical structure included in a brain image and performing registration between a standard brain image and a brain image by combination of registration algorithms using the markers. As the combination of registration algorithms, JP2014-518516A has proposed a method of applying affine registration subsequent to application of rigid registration and further performing B spline registration.

SUMMARY OF THE INVENTION

However, in the method described in JP2014-518516A, it is necessary for the user to search for an anatomical structure in a displayed image and set a marker in the searched anatomical structure. For this reason, the burden on the user's work is heavy. In addition, JP2014-518516A does not specifically describe the anatomical structure, and registration between the brain image and the standard brain image may not be accurately performed depending on the type of anatomical structure in which the marker is set. In addition, in the method described in JP2014-518516A, affine transformation is performed after rigid registration. However, in the method described in JP2014-518516A, the degree of freedom of affine transformation is high, and deformations that are not possible as anatomical structures are also included. For this reason, the affine transformation may unnaturally deform an anatomical structure included in the brain.

The present invention has been made in view of the above circumstances, and it is an object of the present invention to make it possible to more appropriately perform registration between a brain image and a standard brain image.

A medical image processing apparatus according to the present invention comprises: a landmark detection unit that detects at least four reference landmarks of a left eye, a right eye, a diencephalon, a fornix, a corpus callosum, a left hippocampus, and a right hippocampus from a brain image including a brain of a subject; a first registration unit that performs first registration including registration by similarity transformation using the reference landmarks between the brain image and a standard brain image; and a second registration unit that performs second registration by nonlinear transformation between the brain image and the standard brain image after the first registration.

In the medical image processing apparatus according to the present invention, the landmark detection unit may detect the reference landmarks by performing template matching between the brain image and a template including the reference landmarks in the standard brain image.

In the medical image processing apparatus according to the present invention, after registration using the reference landmarks, the first registration unit may perform additional registration between the entire brain image and the entire standard brain image as the first registration.

In the medical image processing apparatus according to the present invention, the landmark detection unit may further detect at least one local landmark from the brain image based on a result of registration using the reference landmarks, and the first registration unit may perform, as the first registration, further registration by similarity transformation between the detected reference landmarks and the detected local landmark and reference landmarks and a local landmark corresponding to the detected reference landmarks and the detected local landmark included in the standard brain image.

A medical image processing method according to the present invention comprises: detecting at least four reference landmarks of a left eye, a right eye, a diencephalon, a fornix, a corpus callosum, a left hippocampus, and a right hippocampus from a brain image including a brain of a subject; performing first registration including registration by similarity transformation using the reference landmarks between the brain image and a standard brain image; and performing second registration by nonlinear transformation between the brain image and the standard brain image after the first registration.

In addition, a program causing a computer to execute the medical image processing method according to the present invention may be provided.

Another medical image processing apparatus according to the present invention comprises: a memory that stores commands to be executed by a computer; and a processor configured to execute the stored commands. The processor executes processing for detecting at least four reference landmarks of a left eye, a right eye, a diencephalon, a fornix, a corpus callosum, a left hippocampus, and a right hippocampus from a brain image including a brain of a subject, performing first registration including registration by similarity transformation using the reference landmarks between the brain image and a standard brain image, and performing second registration by nonlinear transformation between the brain image and the standard brain image after the first registration.

According to the present invention, at least four reference landmarks of the left eye, the right eye, the diencephalon, the fornix, the corpus callosum, the left hippocampus, and the right hippocampus are detected from the brain image including the brain of the subject, the first registration including registration by similarity transformation using reference landmarks between the brain image and the standard brain image is performed, and the second registration is performed by nonlinear transformation between the brain image and the standard brain image after the first registration. For this reason, it is possible to perform registration between the brain image and the standard brain image without at least four anatomical regions of the left eye, the right eye, the diencephalon, the fornix, the corpus callosum, the left hippocampus, and the right hippocampus included in the brain image being unnaturally deformed. Therefore, it is possible to perform registration between the brain image and the standard brain image more appropriately.

BRIEF DESCRIPTION OF THE DRAWINGS

FIG. 7 is a flowchart showing the process performed in the second embodiment.

DESCRIPTION OF THE PREFERRED EMBODIMENTS

Figure 1:
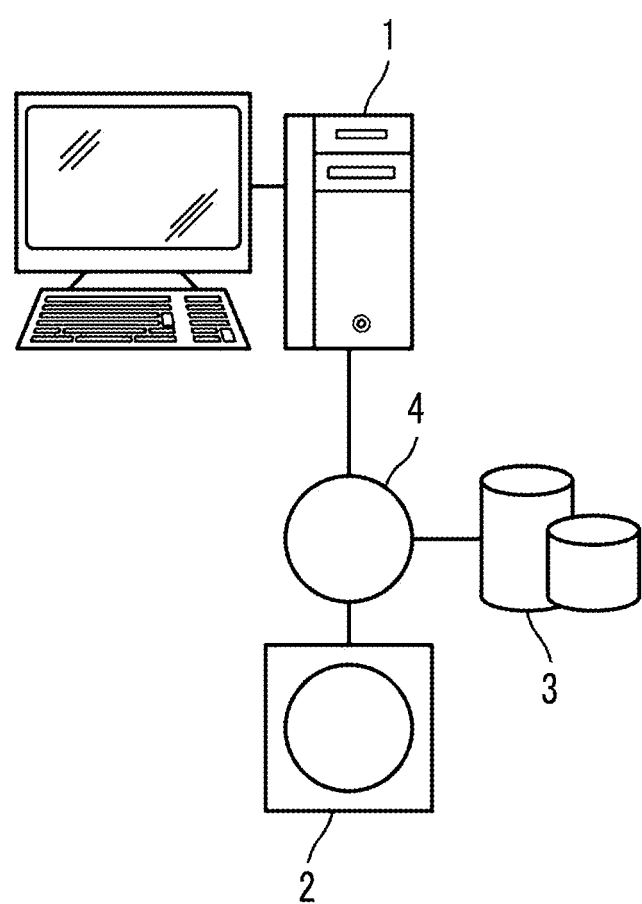
FIG. 1 is a hardware configuration diagram showing an outline of a diagnostic support system to which a medical image processing apparatus according to an embodiment of the present invention is applied.

Hereinafter, embodiments of the present invention will be described with reference to the accompanying diagrams. FIG. 1 is a hardware configuration diagram showing the outline of a diagnostic support system to which a medical image processing apparatus according to a first embodiment of the present invention is applied. As shown in FIG. 1, in the diagnostic support system, a medical image processing apparatus 1 according to the first embodiment, a three-dimensional image capturing apparatus 2, and an image storage server 3 are communicably connected to each other through a network 4.

The three-dimensional image capturing apparatus 2 is an apparatus that generates a three-dimensional medical image showing a part, which is a diagnostic target part of a patient who is a subject, by imaging the part. Specifically, the three-dimensional image capturing apparatus 2 is a CT apparatus, an MRI apparatus, a PET apparatus, or the like. The medical image generated by the three-dimensional image capturing apparatus 2 is transmitted to the image storage server 3 and is stored therein. In the present embodiment, the three-dimensional image capturing apparatus 2 is an MRI apparatus, and an MRI image of the head including the brain of the subject is generated as a three-dimensional brain image.

The image storage server 3 is a computer that stores and manages various kinds of data, and comprises a large-capacity external storage device and software for database management. The image storage server 3 communicates with other apparatuses through the wired or wireless network 4 to transmit and receive image data or the like. Specifically, the image storage server 3 acquires various kinds of data including image data of the medical image, which is generated by the three-dimensional image capturing apparatus 2, through the network, and stores the acquired data in a recording medium, such as a large-capacity external storage device, to manage the acquired data. The storage format of image data and the communication between devices through the network 4 are based on a protocol, such as a digital imaging and communication in medicine (DICOM). In the present embodiment, it is assumed that image data of a plurality of three-dimensional brain images are stored in the image storage server 3. In addition, it is assumed that image data of a standard brain image to be described later is also stored in the image storage server 3.

The medical image processing apparatus 1 is realized by installing a medical image processing program according to the first embodiment on one computer. The computer may be a workstation or a personal computer that is directly operated by a doctor who performs diagnosis, or may be a server computer connected to these through a network. The medical image processing program is distributed in a state in which the medical image processing program is recorded on a recording medium, such as a digital versatile disc (DVD) or a compact disc read only memory (CD-ROM), and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
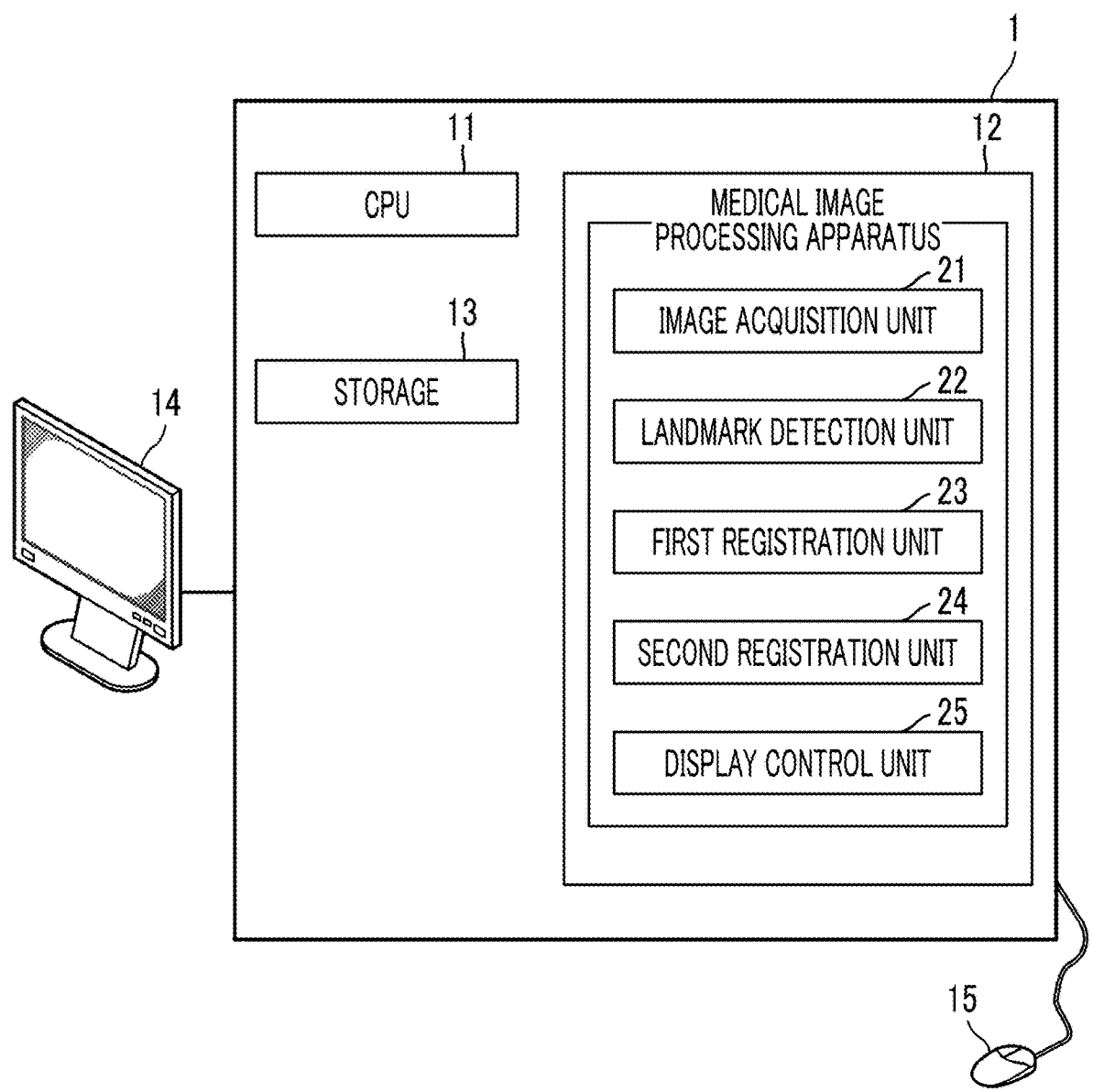
FIG. 2 is a diagram showing the schematic configuration of the medical image processing apparatus.

FIG. 2 is a diagram showing the schematic configuration of a medical image processing apparatus realized by installing a medical image processing program on a computer. As shown in FIG. 2, the medical image processing apparatus 1 comprises a central processing unit (CPU) 11, a memory 12, and a storage 13 as the configuration of a standard workstation. A display 14, such as a liquid crystal display, and an input unit 15, such as a keyboard and a mouse, are connected to the medical image processing apparatus 1.

The storage 13 is a storage device, such as a hard disk or a solid state drive (SSD). A brain image B0 of the subject, a standard brain image Bs, and various kinds of information including information required for processing, which are acquired from the image storage server 3 through the network 4, are stored in the storage 13.

Here, the standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains. The standard brain image Bs may be created by computer graphics or the like. Alternatively, a brain image of one healthy person may be used as the standard brain image Bs.

A medical image processing program is stored in the memory 12. As processing to be executed by the CPU 11, the medical image processing program defines: image acquisition processing for acquiring the brain image B0 including the brain of the subject; landmark detection processing for detecting at least four reference landmarks of the left eye, the right eye, the diencephalon, the fornix, the corpus callosum, the left hippocampus, and the right hippocampus from the brain image; first registration processing including registration by similarity transformation using reference landmarks between the brain image B0 and the standard brain image Bs; and second registration processing by nonlinear transformation between the brain image and the standard brain image Bs after the first registration.

Then, the CPU 11 executes these processes according to the program, so that the computer functions as an image acquisition unit 21, a landmark detection unit 22, a first registration unit 23, and a second registration unit 24. The medical image processing apparatus 1 may comprise a plurality of processors or processing circuits that perform image acquisition processing, landmark detection processing, first registration processing, and second registration processing.

The image acquisition unit 21 acquires the brain image B0 for registration with the standard brain image Bs from the image storage server 3. In a case where the brain image B0 is already stored in the storage 13, the image acquisition unit 21 may acquire the brain image B0 from the storage 13. In the present embodiment, those stored in the image storage server 3 are brain images acquired by imaging the head of the subject, and include structures other than the brain, such as a skull. The image acquisition unit 21 also acquires a standard brain image Bs from the image storage server 3.

Figure 3:
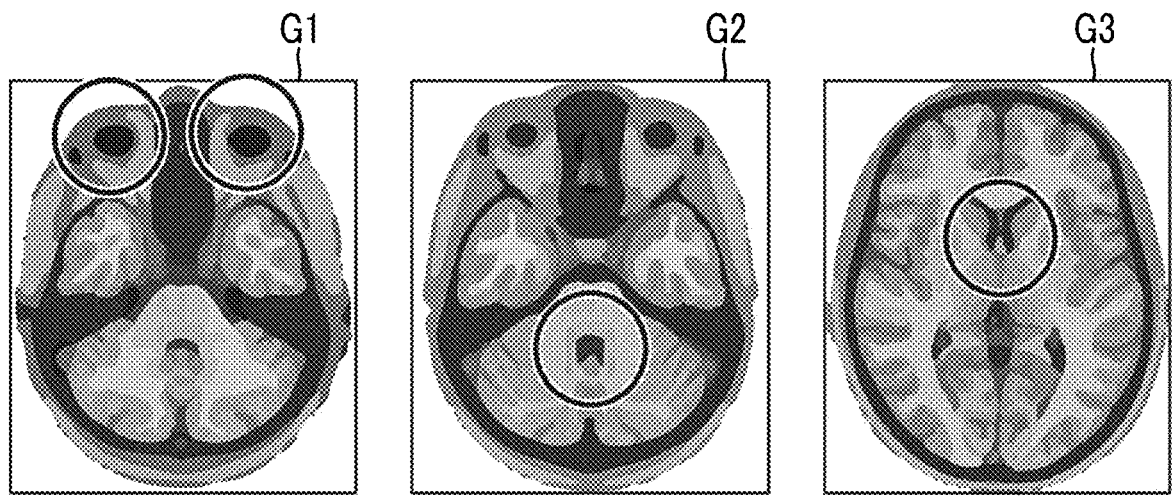
FIG. 3 is a diagram showing slice images on tomographic planes on which the left eye, the right eye, the diencephalon, and the fornix are seen in a brain image.

The landmark detection unit 22 detects at least four reference landmarks among the left eye, the right eye, the diencephalon, the fornix, the corpus callosum, the left hippocampus, and the right hippocampus from the brain image B0. In the present embodiment, four reference landmarks of the left eye, the right eye, the diencephalon, and the fornix are detected. However, the present invention is not limited thereto as long as at least four reference landmarks of the left eye, the right eye, the diencephalon, the fornix, the corpus callosum, the left hippocampus, and the right hippocampus are detected. FIG. 3 is a diagram showing slice images on tomographic planes on which the left eye, the right eye, the diencephalon, and the fornix are seen in the brain image B0. In FIG. 3, a slice image G1 includes the left eye and the right eye, a slice image G2 includes the diencephalon, and a slice image G3 includes the corpus callosum. The left and right eyes, the diencephalon, and the corpus callosum in the respective slice images G1 to G3 are surrounded with a circle.

Here, in the present embodiment, the position of the center of gravity of the reference landmark is detected. However, the pixel position of at the end of the reference landmark, each pixel position on the contour line, or the like may be detected. In addition, the reference landmark region itself, that is, all pixel positions in the reference landmark may be detected.

For detection of the reference landmark, the landmark detection unit 22 comprises a discriminator that is machine-learned so as to detect each of the left eye, the right eye, the diencephalon, and the fornix. For the machine learning, any method (for example, Ada-Boost) is used. In the standard brain image Bs, it is assumed that the positions of the four reference landmarks of the left eye, the right eye, the diencephalon, and the fornix are already detected and stored in the storage 13.

Here, the detection of the reference landmark may be performed on the three-dimensional brain image B0, but may be performed on the slice image of the brain image B0. In this case, the slice image may be a slice image of any of a sagittal section, a coronal section, and an axial section.

After the reference landmark is detected by the discriminator, template matching may be performed in the peripheral region of the detected reference landmark. In this case, a template obtained by extracting each region of the left eye, the right eye, the diencephalon, and the fornix from the standard brain image Bs is stored in the storage 13. Then, the landmark detection unit 22 performs template matching between each template of the left eye, the right eye, the diencephalon, and the fornix and the peripheral region of the reference landmark detected in the brain image B0. In this manner, the reference landmark in the brain image B0 can be detected more accurately. On the other hand, the reference landmark may be detected only by template matching without using a discriminator.

The first registration unit 23 performs first registration including registration by similarity transformation using reference landmarks between the brain image B0 and the standard brain image Bs. Specifically, registration is performed by similarity transformation between the reference landmark detected by the landmark detection unit 22 and the reference landmark corresponding to the detected reference landmark in the standard brain image Bs. Here, it is assumed that the positions of the four reference landmarks detected from the brain image B0 in the brain image B0 are Pt1, Pt2, Pt3, and Pt4 and the positions of the reference landmarks in the standard brain image Bs corresponding to the detected reference landmarks are expressed as Ps1, Ps2, Ps3, and Ps4. In addition, in the following description, it is assumed that Pt1, Pt2, Pt3, and Pt4 are used as reference numerals of the reference landmarks detected from the brain image B0 and Ps1, Ps2, Ps3, and Ps4 are used as reference numerals of the reference landmarks in the standard brain image Bs. The first registration unit 23 calculates coefficients of similarity transformation between the reference landmarks Pt1, Pt2, Pt3, and Pt4 in the brain image B0 and the reference landmarks Ps1, Ps2, Ps3, and Ps4 in the standard brain image Bs using the following Expression (1). Expression (1) means calculating a coefficient that minimizes the value in Σ. In Expression (1), the position of the reference landmark in the brain image B0 is indicated by Pti (i=1 to 4), and the position of the reference landmark in the standard brain image Bs is indicated by Psi. In practice, however, the position of the reference landmark in the brain image B0 and the position of the reference landmark in the standard brain image Bs have three-dimensional coordinate values.

$$\sum_{i=1}^{4}(Pti - \qquad\qquad\qquad\qquad\qquad\qquad\text{[Expression 1]}$$

$$(S(S_x, S_y, S_z)R(\theta_x, \theta_y, \theta_z)Psi + T(t_x, t_y, t_z))^2 \to \min$$

Here, the coefficients calculated in Expression (1) are $S(s_x, s_y, s_z)$, $R(\theta_x, \theta_y, \theta_z)$, and $T(t_x, t_y, t_z)$. $S(s_x, s_y, s_z)$ is a scaling matrix indicating enlargement and reduction in the x, y, and z directions, $R(\theta_x, \theta_y, \theta_z)$ is a three-dimensional rotation matrix, and $T(t_x, t_y, t_z)$ is a three-dimensional movement matrix (vector).

The first registration unit 23 performs the first registration by performing similarity transformation on the brain image B0 so that the brain image B0 matches the standard brain image Bs. That is, using the coefficients $S(s_x, s_y, s_z)$, $R(\theta_x, \theta_y, \theta_z)$, and $T(t_x, t_y, t_z)$ calculated by Expression (1), the brain image B0 is subjected to similarity transformation to perform the first registration. In order to accurately calculate the scaling matrix S, the rotation matrix R, and the movement vector T, at least four reference landmarks are required. In a case where there are three reference landmarks, for example, a scaling matrix indicating enlargement and reduction in the normal direction with respect to the plane formed by the three reference landmarks is not accurately determined, and the accuracy of registration is reduced. In addition, these at least four reference landmarks should not be on the same plane at the same time.

Figure 4:
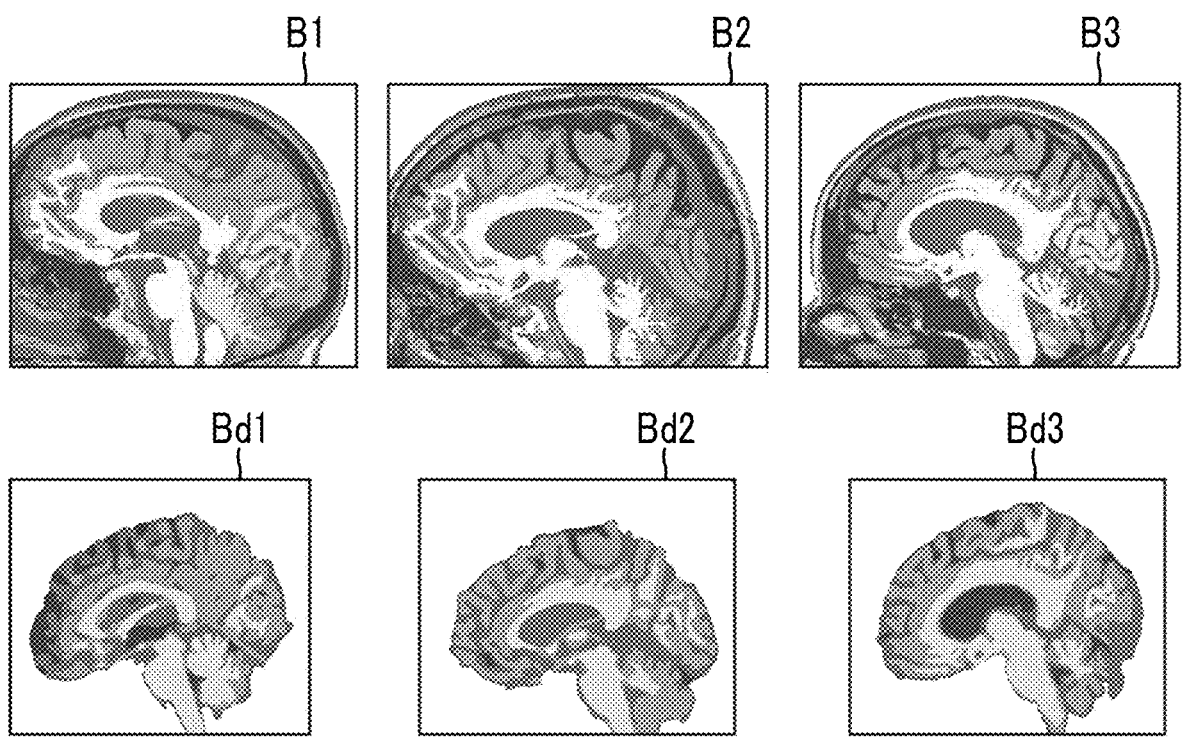
FIG. 4 is a diagram showing a brain image that is registrated with a standard brain image by first registration.

FIG. 4 is a diagram showing a brain image that is registrated with a standard brain image by the first registration. As a result of the first registration, as shown in FIG. 4, three brain images B1 to B3 are registrated with the standard brain image Bs, and brain images Bd1 to Bd3 after the first registration are generated. The brain images Bd1 to Bd3 after the first registration have substantially the same position and the same shape and size as the reference landmarks. In the brain images Bd1 to Bd3 after the first registration in FIG. 4, only the brain region is extracted. In addition, FIG. 4 shows slice images on the sagittal sections of the brain image and the registrated brain images. Here, as shown in FIG. 4, by the first registration, the brain image B0 does not completely match the standard brain image Bs.

The second registration unit 24 performs second registration by nonlinear transformation between the brain image B1 and the standard brain image Bs after the first registration. As the registration by nonlinear transformation, for example, it is possible to use registration performed by converting pixel positions using nonlinear functions, such as B spline and thin plate spline, or registration using nonlinear transformation using diffeomorphc. In the second registration, these different nonlinear transformations may be combined. In the present embodiment, it is assumed that, after performing registration by nonlinear transformation using a B spline function, registration by nonlinear transformation using diffeomorphc is performed. In this case, the first registration result calculated by the first registration unit 23 may be used as an initial value of registration by nonlinear transformation using a B spline function. In addition, the result of registration by nonlinear transformation using a B spline function may be used as an initial value of registration by nonlinear transformation using diffeomorphc.

As the second registration, registration may be performed first by nonlinear transformation using a thin plate spline with the first registration result as an initial value, and then nonlinear transformation using a B spline function may be performed with the result of registration by nonlinear transformation using a thin plate spline as the initial value. In this case, nonlinear transformation using diffeomorphc may be further performed. By performing the second registration in this manner, the brain image B0 can be matched with the standard brain image Bs more accurately.

Figure 5:
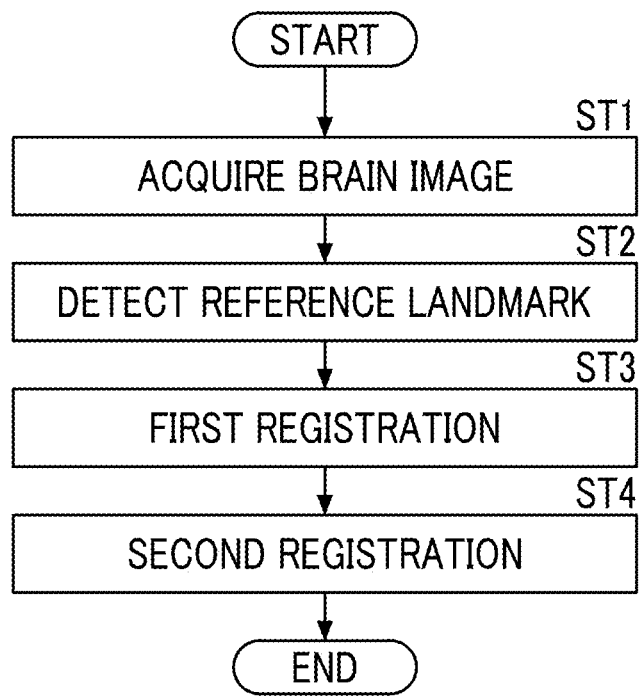
FIG. 5 is a flowchart showing the process performed in the first embodiment.

Next, the process performed in the first embodiment will be described. FIG. 5 is a flowchart showing the process performed in the first embodiment. It is assumed that the standard brain image Bs is acquired from the image storage server 3 and stored in the storage 13. First, the image acquisition unit 21 acquires the brain image B0 that is a registration target (step ST1). Then, the landmark detection unit 22 detects at least four reference landmarks among the left eye, the right eye, the diencephalon, the fornix, the corpus callosum, the left hippocampus, and the right hippocampus from the brain image B0 (step ST2).

Then, the first registration unit 23 performs first registration including registration by similarity transformation using reference landmarks between the brain image B0 and the standard brain image Bs (step ST3). Then, the second registration unit 24 performs second registration by nonlinear transformation between the brain image and the standard brain image Bs after the first registration (step ST4), and the process ends. The brain image after registration is provided for calculation of the atrophy rate of the brain and the like.

As described above, according to the first embodiment, at least four reference landmarks of the left eye, the right eye, the diencephalon, the fornix, the corpus callosum, the left hippocampus, and the right hippocampus are detected from the brain image B0 including the brain of the subject, the first registration including registration by similarity transformation using reference landmarks between the brain image B0 and the standard brain image Bs is performed, and the second registration is performed by nonlinear transformation between the brain image and the standard brain image Bs after the first registration. For this reason, it is possible to perform registration between the brain image B0 and the standard brain image Bs without at least four anatomical regions of the left eye, the right eye, the diencephalon, the fornix, the corpus callosum, the left hippocampus, and the right hippocampus included in the brain image B0 being unnaturally deformed. Therefore, it is possible to perform registration between the brain image B0 and the standard brain image Bs more appropriately.

Next, a second embodiment of the present invention will be described. The configuration of a medical image processing apparatus according to the second embodiment is the same as the configuration of the medical image processing apparatus according to the first embodiment described above, and only the processing to be performed is different. Accordingly, the detailed description of the apparatus will be omitted herein. The second embodiment is different from the first embodiment in that the landmark detection unit 22 further detects at least one local landmark from the brain image B0 based on the result of registration using the reference landmark and the first registration unit 23 performs further registration by similarity transformation between the reference landmark and the local landmark detected from the brain image B0 and the reference landmark and the local landmark corresponding to the detected reference landmark and local landmark included in the standard brain image Bs as the first registration.

Figure 6:
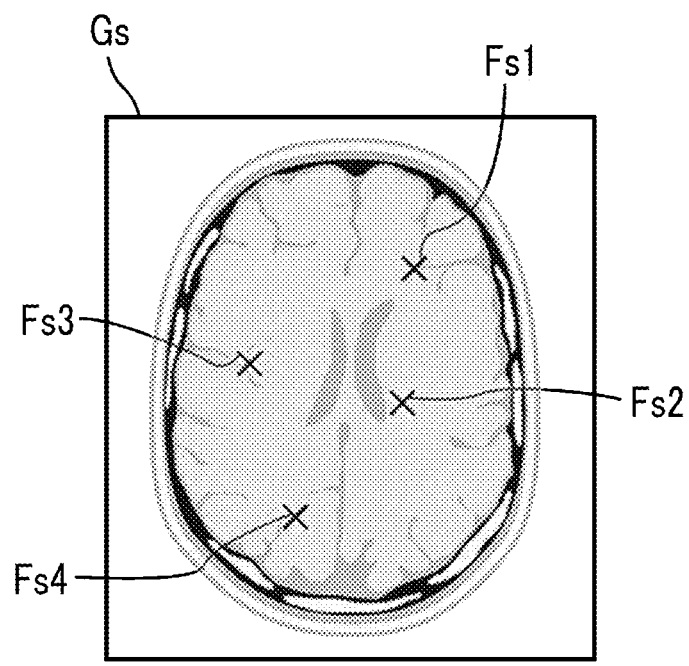
FIG. 6 is a diagram showing a slice image of a standard brain image in which local landmarks are set.

In the second embodiment, the landmark detection unit 22 further detects at least one local landmark different from the reference landmark based on the registration result using the reference landmark in the first embodiment. FIG. 6 is a diagram showing a slice image Gs of the standard brain image Bs for explaining the detection of a local landmark. In the second embodiment, as shown in FIG. 6, local landmarks Fsi other than the left eye, the right eye, diencephalon, the fornix, the corpus callosum, the left hippocampus, and the right hippocampus are set in the slice image Gs of the standard brain image Bs. As the local landmark Fsi, for example, a sulcus, an end of the sulcus, a cerebral ventricle, and the like can be used. In FIG. 6, four local landmarks Fs1 to Fs4 are set. In the second embodiment, a local region including the local landmark Fsi of the standard brain image Bs is stored in the storage 13 as a template.

In the second embodiment, the landmark detection unit 22 sets the position Fpti of a temporary local landmark corresponding to the local landmark Fsi in the brain image B0 by mapping the local landmark Fsi set in the standard brain image Bs to the brain image B0 based on the following Expression (2) using the result of registration using the reference landmark, that is, the coefficient calculated by the above Expression (1).

$$\text{Fpti} = S(S_x, S_y, S_z) R(\theta_x, \theta_y, \theta_z) \text{Fsi} + T(t_x, t_y, t_z) \quad \text{[Expression 2]}$$

Then, the landmark detection unit 22 performs template matching between the template of a local region including the local landmark Fsi set in the standard brain image Bs and the peripheral region of the temporary local landmark Fpti set in the brain image B0. As a result, the landmark detection unit 22 detects the accurate position Fti of the local landmark corresponding to the local landmark Fsi. In addition, it is assumed that the reference numeral Fti may also be used for the local landmark in the brain image B0.

Here, the detection of the local landmark Fti may be performed on the three-dimensional brain image B0, but may be performed on the slice image of the brain image B0. In this case, the slice image may be a slice image of any of a sagittal section, a coronal section, and an axial section.

In the second embodiment, the first registration unit 23 performs further registration by similarity transformation between the reference landmark and the local landmark detected from the brain image B0 and the reference landmark and the local landmark corresponding to the detected reference landmark and local landmark included in the standard brain image Bs. Specifically, using the following Expression (3), coefficients of similarity transformation between the reference landmarks Pt1, Pt2, Pt3, and Pt4 and the local landmark Fti in the brain image B0 and the reference landmarks Ps1, Ps2, Ps3, and Ps4 and the local landmark Fsi in the standard brain image Bs are calculated. Expression (3) means calculating a coefficient that minimizes the sum of values in Σ. Also in Expression (3), the position of the reference landmark in the brain image B0 is indicated Pti, the position of the local landmark in the brain image B0 is indicated by Fti, the position of the reference landmark in the standard brain image Bs is indicated by Psi, and the position of the local landmark in the standard brain image Bs is indicated by Fsi. In practice, however, the position of the reference landmark in the brain image B0, the position of the local landmark in the brain image B0, the position of the reference landmark in the standard brain image Bs, and the position of the local landmark in the standard brain image Bs have three-dimensional coordinate values.

$$\sum_{i=1}^{4} (Pti - (S1(S_x, S_y, S_z) R1(\theta_x, \theta_y, \theta_z) Psi + T1(t_x, t_y, t_z))^2 + \sum_{i=1}^{n} (Fti - (S2(S_x, S_y, S_z) R2(\theta_x, \theta_y, \theta_z) Fsi + T2(t_x, t_y, t_z))^2 \to \min \quad \text{[Expression 3]}$$

Here, the coefficients calculated in Expression (3) are $S1(s_x, s_y, s_z)$, $R1(\theta_x, \theta_y, \theta_z)$, $T1(t_x, t_y, t_z)$, $S2(s_x, s_y, s_z)$, $R2(\theta_x, \theta_y, \theta_z)$ and $T2(t_x, t_y, t_z)$. $S1(s_x, s_y, s_z)$ is a scaling matrix indicating enlargement and reduction in the x, y, and z directions for the reference landmark, $R1(\theta_x, \theta_y, \theta_z)$ is a three-dimensional rotation matrix for the reference landmark, and $T1(t_x, t_y, t_z)$ is a three-dimensional movement matrix for the reference landmark. $S2(s_x, s_y, s_z)$ is a scaling matrix indicating enlargement and reduction in the x, y, and z directions for the local landmark, $R2(\theta_x, \theta_y, \theta_z)$ is a three-dimensional rotation matrix for the local landmark, and $T2(t_x, t_y, t_z)$ is a three-dimensional movement matrix for the local landmark.

In the second embodiment, the first registration unit 23 perform the first registration between the brain image B0 and the standard brain image Bs based on the result of the further registration. That is, the brain image B0 is subjected to similarity transformation by the coefficients $S1(s_x, s_y, s_z)$, $R1(\theta_x, \theta_y, \theta_z)$, $T1(t_x, t_y, t_z)$, $S2(s_x, s_y, s_z)$, $R2(\theta_x, \theta_y, \theta_z)$, and $T2(t_x, t_y, t_z)$ calculated by Expression (3), thereby performing the first registration.

Next, the process performed in the second embodiment will be described. FIG. 7 is a flowchart showing the process performed in the second embodiment. It is assumed that the standard brain image Bs is acquired from the image storage server 3 and stored in the storage 13. First, the image acquisition unit 21 acquires the brain image B0 to be normalized (step ST11). Then, the landmark detection unit 22 detects at least four reference landmarks among the left eye, the right eye, the diencephalon, the fornix, the corpus callosum, the left hippocampus, and the right hippocampus from the brain image B0 (step ST12).

Then, the first registration unit 23 performs registration by similarity transformation using reference landmarks between the brain image B0 and the standard brain image Bs, and acquires the result of the registration using the reference landmarks (step ST13). Then, the landmark detection unit 22 detects a local landmark from the brain image B0 based on the result of registration using the reference landmark (step ST14).

Then, as the first registration, the first registration unit 23 performs further registration by similarity transformation between the reference landmark and the local landmark detected by the landmark detection unit 22 and the reference landmark and the local landmark corresponding to the detected reference landmark and local landmark in the standard brain image Bs (step ST15). Then, the second registration unit 24 performs second registration by nonlinear transformation between the brain image and the standard brain image Bs after the first registration (step ST16), and the process ends. The brain image after registration is provided for diagnosis, such as calculation of the atrophy rate of the brain.

In the first and second embodiments described above, after performing the first registration, additional registration for matching the entire brain image B0, that is, the shape and size of the brain image B0 with the shape and size of the standard brain image Bs may be further performed. In the additional registration, the first registration unit 23 calculates an additional coefficient for matching the shape and size of the brain image B0 with the shape and size of the standard brain image Bs. In this case, the first registration unit 23 registrates the brain image B0 with the standard brain image Bs by further using the additional coefficient. In this manner, it is possible to accurately match the shape and size of the brain with the standard brain image Bs in addition to the anatomical region included in the brain image B0.

In the first and second embodiments described above, the MRI image of the subject is used as a brain image. However, medical images other than the MRI image, such as a CT image and a PET image, may be used as brain images.

Hereinafter, the effect of the present embodiment will be described.

By detecting the reference landmark by performing template matching between the brain image and the template including the reference landmark in the standard brain image, it is possible to accurately detect the reference landmark.

By further detecting at least one local landmark from the brain image based on the result of registration using the reference landmark and performing, as the first registration, further registration by similarity transformation between the detected reference landmark and the detected local landmark and the reference landmark and the local landmark corresponding to the detected reference landmark and the detected local landmark included in the standard brain image Bs, it is possible to more accurately normalize the brain.

By performing additional registration between the entire brain image and the entire standard brain image after registration, it is also possible to accurately match the shape and size of the brain with the standard brain image in addition to at least four anatomical regions of the left eye, the right eye, the diencephalon, the fornix, the corpus callosum, the left hippocampus, and the right hippocampus included in the brain and its periphery.

EXPLANATION OF REFERENCES

1: brain image processing apparatus
2: three-dimensional image capturing apparatus
3: image storage server
4: network
11: CPU
12: memory
13: storage
14: display
15: input unit
21: image acquisition unit
22: landmark detection unit
23: first registration unit
24: second registration unit
B1 to B3: brain image
Bd1 to Bd3: brain image afters registration
Bs: standard brain image
Fs1 to Fs4: local landmark
G1 to G3, Gs: slice image

What is claimed is:

1. A medical image processing apparatus, comprising a processor configured to:
   detect at least four reference landmarks of a left eye, a right eye, a diencephalon, a fornix, a corpus callosum, a left hippocampus, and a right hippocampus from a brain image including a brain of a subject;
   perform first registration including registration by similarity transformation using the reference landmarks between the brain image and a standard brain image; and
   perform second registration by nonlinear transformation between the brain image and the standard brain image after the first registration,
   wherein the second registration by the nonlinear transformation is performed with a first registration result as an initial value,
   wherein, after the registration by similarity transformation using the reference landmarks, the processor configured to perform additional registration between the entire brain image and the entire standard brain image as the first registration,
   wherein the additional registration calculates an additional coefficient for matching the shape and size of the brain image with the shape and size of the standard brain image.

2. The medical image processing apparatus according to claim 1,
   wherein the processor configured to detect the reference landmarks by performing template matching between the brain image and a template including the reference landmarks in the standard brain image.

3. The medical image processing apparatus according to claim 2,
   wherein, after the registration by similarity transformation using the reference landmarks, the processor configured to perform additional registration between the entire brain image and the entire standard brain image as the first registration.

4. The medical image processing apparatus according to claim 1,
   wherein the processor further configured to detect at least one local landmark from the brain image based on a result of the registration by similarity transformation using the reference landmarks, and perform, as the first registration, further registration by similarity transformation between the detected reference landmarks and the detected local landmark, and reference landmarks and a local landmark corresponding to the detected reference landmarks and the detected local landmark included in the standard brain image.

5. The medical image processing apparatus according to claim 2, wherein the processor further configured to detect at least one local landmark from the brain image based on a result of the registration by similarity transformation using the reference landmarks, and perform, as the first registration, further registration by similarity transformation between the detected reference landmarks and the detected local landmark, and reference landmarks and a local landmark corresponding to the detected reference landmarks and the detected local landmark included in the standard brain image.

6. The medical image processing apparatus according to claim 1, wherein the processor further configured to detect at least one local landmark from the brain image based on a result of the registration by similarity transformation using the reference landmarks, and perform, as the first registration, further registration by similarity transformation between the detected reference landmarks and the detected local landmark, and reference landmarks and a local landmark corresponding to the detected reference landmarks and the detected local landmark included in the standard brain image.

7. The medical image processing apparatus according to claim 3, wherein the processor further configured to detect at least one local landmark from the brain image based on a result of the registration by similarity transformation using the reference landmarks, and perform, as the first registration, further registration by similarity transformation between the detected reference landmarks and the detected local landmark, and reference landmarks and a local landmark corresponding to the detected reference landmarks and the detected local landmark included in the standard brain image.

8. A medical image processing method, comprising:

detecting at least four reference landmarks of a left eye, a right eye, a diencephalon, a fornix, a corpus callosum, a left hippocampus, and a right hippocampus from a brain image including a brain of a subject;

performing first registration including registration by similarity transformation using the reference landmarks between the brain image and a standard brain image; and performing second registration by nonlinear transformation between the brain image and the standard brain image after the first registration, wherein the second registration by the nonlinear transformation is performed with a first registration result as an initial value, wherein, after the registration by similarity transformation using the reference landmarks, additional registration between the entire brain image and the entire standard brain image is performed as the first registration, wherein the additional registration calculates an additional coefficient for matching the shape and size of the brain image with the shape and size of the standard brain image.

9. The medical image processing method according to claim 8, wherein the reference landmarks is detect by performing template matching between the brain image and a template including the reference landmarks in the standard brain image.

10. The medical image processing method according to claim 9, wherein, after the registration by similarity transformation using the reference landmarks, additional registration between the entire brain image and the entire standard brain image is performed as the first registration.

11. The medical image processing method according to claim 8, wherein at least one local landmark from the brain image based on a result of the registration by similarity transformation using the reference landmarks is detected and further registration by similarity transformation between the detected reference landmarks and the detected local landmark, and reference landmarks and a local landmark is performed as the first registration, the reference landmarks and the local landmark corresponding to the detected reference landmarks and the detected local landmark included in the standard brain image.

12. The medical image processing method according to claim 9, wherein at least one local landmark from the brain image based on a result of the registration by similarity transformation using the reference landmarks is detected and further registration by similarity transformation between the detected reference landmarks and the detected local landmark, and reference landmarks and a local landmark is performed as the first registration, the reference landmarks and the local landmark corresponding to the detected reference landmarks and the detected local landmark included in the standard brain image.

13. The medical image processing method according to claim 8, wherein at least one local landmark from the brain image based on a result of the registration by similarity transformation using the reference landmarks is detected and further registration by similarity transformation between the detected reference landmarks and the detected local landmark, and reference landmarks and a local landmark is performed as the first registration, the reference landmarks and the local landmark corresponding to the detected reference landmarks and the detected local landmark included in the standard brain image.

14. The medical image processing method according to claim 10, wherein at least one local landmark from the brain image based on a result of the registration by similarity transformation using the reference landmarks is detected and further registration by similarity transformation between the detected reference landmarks and the detected local landmark, and reference landmarks and a local landmark is performed as the first registration, the reference landmarks and the local landmark corresponding to the detected reference landmarks and the detected local landmark included in the standard brain image.

15. A non-transitory computer readable medium for storing a medical image processing program causing a computer to execute a process comprising:
   detecting at least four reference landmarks of a left eye, a right eye, a diencephalon, a fornix, a corpus callosum, a left hippocampus, and a right hippocampus from a brain image including a brain of a subject;
   performing first registration including registration by similarity transformation using the reference landmarks between the brain image and a standard brain image; and
   performing second registration by nonlinear transformation between the brain image and the standard brain image after the first registration,
   wherein the second registration by the nonlinear transformation is performed with a first registration result as an initial value,
   wherein, after the registration by similarity transformation using the reference landmarks, additional registration between the entire brain image and the entire standard brain image is performed as the first registration,
   wherein the additional registration calculates an additional coefficient for matching the shape and size of the brain image with the shape and size of the standard brain image.

* * * * *